(12) United States Patent
Yaroshenko et al.

(10) Patent No.: US 11,154,264 B2
(45) Date of Patent: Oct. 26, 2021

(54) SINGLE SHOT X-RAY PHASE-CONTRAST AND DARK FIELD IMAGING

(71) Applicant: KONINKLIJKE PHILIPS N.V., Eindhoven (NL)

(72) Inventors: Andriy Yaroshenko, Garching (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/772,485

(22) PCT Filed: Dec. 11, 2018

(86) PCT No.: PCT/EP2018/084253
§ 371 (c)(1),
(2) Date: Jun. 12, 2020

(87) PCT Pub. No.: WO2019/115483
PCT Pub. Date: Jun. 20, 2019

(65) Prior Publication Data
US 2020/0397393 A1   Dec. 24, 2020

(30) Foreign Application Priority Data
Dec. 15, 2017  (EP) .................................... 17207719

(51) Int. Cl.
*A61B 6/00* (2006.01)
*G01N 23/041* (2018.01)
(Continued)

(52) U.S. Cl.
CPC ............ *A61B 6/484* (2013.01); *A61B 6/4291* (2013.01); *G01N 23/041* (2018.02);
(Continued)

(58) Field of Classification Search
CPC .... A61B 6/484; A61B 6/4291; G01N 23/041; G01N 23/083; G01N 2223/04;
(Continued)

(56) References Cited

U.S. PATENT DOCUMENTS 9,675,276 B2   6/2017  Gopinathan
2010/0322380 A1  12/2010  Baeumer
(Continued)

FOREIGN PATENT DOCUMENTS

DE   10206020 A1   8/2003
WO   WO2012052900 A1   4/2012
(Continued)

OTHER PUBLICATIONS

PCT International Search Report, International Application No. PCT/EP2018/084253, dated Feb. 25, 2019.
(Continued)

*Primary Examiner* — Blake C Riddick
(74) *Attorney, Agent, or Firm* — Larry Liberchuk

(57) ABSTRACT

A component (XS) for an X-ray detector device (XD), comprising a layer (SL) tessellated in a plurality of different regions (Rj), the regions having respective periodic structures at a respective phase, wherein two neighboring regions have periodic structures at different phases.

12 Claims, 5 Drawing Sheets

(51) Int. Cl.
*G01N 23/083* (2018.01)
*G01T 1/20* (2006.01)
*G01T 1/202* (2006.01)
*G01T 1/24* (2006.01)

(52) U.S. Cl.
CPC .......... *G01N 23/083* (2013.01); *G01T 1/202* (2013.01); *G01T 1/2018* (2013.01); *G01T 1/24* (2013.01); *G01N 2223/04* (2013.01); *G01N 2223/40* (2013.01); *G01N 2223/505* (2013.01)

(58) Field of Classification Search
CPC .......... G01N 2223/40; G01N 2223/505; G01T 1/2018; G01T 1/202; G01T 1/24
See application file for complete search history.

(56) References Cited

U.S. PATENT DOCUMENTS

| | | | |
|---|---|---|---|
| 2011/0243382 A1* | 10/2011 | Morton | A61B 6/463 382/103 |
| 2012/0104262 A1 | 5/2012 | Wiegert | |
| 2013/0137963 A1 | 5/2013 | Olson | |
| 2013/0156284 A1* | 6/2013 | Koehler | A61B 6/484 382/131 |
| 2013/0208864 A1* | 8/2013 | Rossi | G21K 1/067 378/62 |
| 2014/0177795 A1 | 6/2014 | Spahn | |
| 2015/0131783 A1 | 5/2015 | Sato | |
| 2015/0243397 A1* | 8/2015 | Yun | G21K 1/02 378/36 |
| 2016/0196666 A1 | 7/2016 | Vankatraghavan | |
| 2018/0182131 A1 | 6/2018 | Koehler | |

FOREIGN PATENT DOCUMENTS

| | | |
|---|---|---|
| WO | WO2016096622 A1 | 6/2016 |
| WO | WO2017207734 A1 | 12/2017 |

OTHER PUBLICATIONS

Pfeiffer F. et al., "Hard-X-Ray Dark-Field Imaging Using a Grating Interferometer", Nature Materials, vol. 7, No. 2, Jan. 13, 2008 (Jan. 13, 2008), pp. 134-137.

Von Teuffenbach et al., "Grating Based Phase-Contrast and Dark-Field Computed Tomography: A Single-Shot Method", published online, Nature Scientific Reports, 7:7476, Aug. 7, 2017.

Zanette I. et al., "Trimodal Low-Dose X-Ray Tomography", PNAS, vol. 109, No. 26, pp. 10199-102004, Jun. 2012.

Olivio A. et al., "A Coded-Aperture Technique Allowing X-Ray Phase Contrast Imaging with Conventional Sources", Applied Physics Letters Letters 91, 2007.

Hansen P. C. et al., "Exploiting Residual Information in the Parameter Choice for Discrete Ill-Posed Problems", BIT Numerical Mathematics, vol. 46, Issue 1, pp. 41-59, Mar. 2006.

Pfeiffer F. et al., "Phase Retrieval and Differential Phase-Contrast Imaging with Low-Brilliance X-Ray Sources", Nature Physics, vol. 2, pp. 258-261, Apr. 2006.

Yongshuai G. et al., "Fast Data Acquisition Method in X-Ray Differential Phase Contrast Imaging Using a New Grating Design", SPIE Medical Imaging, International Society for Optics and Photonics, 2014.

* cited by examiner

SINGLE SHOT X-RAY PHASE-CONTRAST AND DARK FIELD IMAGING

FIELD OF THE INVENTION

The invention relates to a signal processing system, to a signal processing method, to an imaging arrangement, to a computer program product, and to a computer readable medium.

BACKGROUND OF THE INVENTION

For radiography acquisitions of X-ray phase-contrast and dark-field imaging with a grating interferometer, a sequence of images is necessary that is acquired with different relative grating positions as proposed by F. Pfeiffer et al, "Hard-X-ray dark-field imaging using a grating interferometer", in "Nature materials", vol 7, pp 134-137, February 2008. This makes it necessary to move at least one of the gratings during the image acquisition. However, this makes image acquisition a cumbersome procedure and significantly increases image acquisition time.

X-ray phase-contrast and dark-field imaging in tomography setting presents also with challenges. In particular, it is the rotational motion in tomographic acquisitions that makes the acquisition challenging. The situation has improved with the so-called "sliding window acquisition", where at each projection angle, only one particular relative grating position is acquired and with a recent reconstruction scheme which may be called intensity based iterative reconstruction (IB-SIR) as reported by M. von Teuffenbach et al, "Grating-based phase-contrast and dark-field computed tomography: a single-shot method", published online, Nature Scientific Reports, 7:7476, 7 Aug. 2017. The sliding window acquisition scheme was reported by I. Zanette at al, "Trimodal low-dose X-ray tomography", PNAS, vol 109, No 26, pp 10199-102004, June 2012. However, even in these schemes, some phase stepping is still needed during the acquisition which is at the expense of noise robustness.

WO 2017/207734 A1 discloses an X-ray imaging apparatus having a plurality of X-ray sources and a detector comprising periodic structures having a phase.

SUMMARY OF THE INVENTION

There may therefore be a need in the art to improve noise robustness in phase contrast and/or dark-field imaging.

The object of the present invention is solved by the subject matter of the independent claims where further embodiments are incorporated in the dependent claims.

It should be noted that the following described aspect of the invention equally applies to the image processing method, to the imaging arrangement, to the computer program product, and to the computer readable medium.

According to a first aspect of the invention, there is provided a component for an X-ray detector device, comprising a layer tessellated in a plurality of different regions, the regions having respective periodic structures at a respective phase, wherein two neighboring regions have periodic structures at different phases.

More specifically and according to one embodiment, any two neighboring regions have periodic structures at different phases.

According to one embodiment, at least one (preferably any) given region is at least partly (preferably wholly) surrounded by regions having different phases and each of the different phases is different from the phase of the given region.

At least one of the regions covers a single detector pixel or a group of such pixels.

According to one embodiment, the component is (partly) radiation sensitive, in particular X-radiation sensitive. More specifically and according to one embodiment, the layer is a scintillation layer of an indirect conversion detector or a semi-conductor layer of a direct conversion detector, or other. Instead, as another alternative, the layer may be sensitive to light, for instance a photodiode layer of the indirect conversion type layer.

According to one embodiment, the periodic structures are arranged as an alternating pattern of radiation (in partial X-radiation) sensitive and radiation (in partial X-radiation) insensitive (that is, non-sensitive) elements. The elements may be formed by lithography and etching, laser cutting or any other suitable forming technique, such as 3D printing. In the embodiment where the layer is a scintillation layer, the elements may include scintillating elements and non-scintillating elements.

The regions of different phases (or phase regions) as proposed herein define a spatial structuring of the radiation sensitive component, in particular one or more of its layers. The structuring is such that underlying detector pixels can simultaneously capture intensities as seen through the periodic structures of different phases. This allows efficient signal processing of the captured intensities into phase-contrast- and/or dark-field- and/or transmission imagery.

The regions may be organized into super-regions. The number of regions in each super-region defines the number of neighboring regions for each image pixel. For each imaging pixel there is super-region, such that each region has a different phase. The super-regions are conceptual and define a specific sampling pattern. A grabber is used to implement this. The grabber may be reconfigurable so that the size of super-region may be changed (in particular reduced) upfront or during processing. The size may remain constant or may be varied for any given processing.

The proposed structuring into multi-phase regions integrated in the detector is capable of affording the following advantages for tomographic or radiography imaging. For radiographic imaging, the proposed structured X-ray component allows limiting cross-talk of the pixels to significantly improve the image noise quality for X-ray phase-contrast and dark-field modality. This is achieved because the structured pixilated X-ray component of the detector allows single exposure acquisitions thanks to regions whose periodicities are at different phases. In tomographic imaging, the proposed component allows more robust data acquisition, in particular when combined with IBSIR (intensity based iterative reconstruction), such as disclosed in the paper by M. von Teuffenbach at el as referenced above. In particular, an angular phase stepping of a sliding window acquisition can be complementing with a spatial phase stepping across adjacent pixels thanks to the proposed X-ray component.

According to another aspect, there is provided an X-ray detector device comprising a component as per any one the above described embodiment.

According to another aspect, there is provided an X-ray imaging apparatus comprising the X-ray detector device or a component as per any one of the above described embodiments.

According to another aspect, there is provided a signal processing method for dark-field and/or phase contrast imaging and/or transmission imaging, comprising: receiving readings from an X-ray imaging apparatus having, within an imaging path, a plurality of periodic structures with at least one interface; and processing the readings into dark-field and/or phase-contrast and/or transmission image signals, said processing including a regularization. The processing is formulated as an optimization problem in terms of a cost function. The regularization is formulated as a distinct functional component added to the cost function. The cost regularization is configured to enforce a smoothness property of changes in one, two or all of the three imaging variables (also referred herein as "channels") for the phase contrast, dark-field and transmission. The respective changes may be modelled in terms of a gradient expression per channel.

According to one embodiment, the interfacing periodic structures have different phases.

According to another aspect, there is provided a processing unit configured to perform the method.

According to another aspect, there is provided an imaging apparatus including or communicatively coupled to the processing unit.

According to another aspect, there is provided a computer program element, which, when being executed by at least one processing unit, is adapted to cause the processing unit to perform the method.

According to another aspect, there is provided a computer readable medium having stored thereon the program element.

According to another aspect, there is provided a computer program element, which, when being executed by at least one processing unit, is adapted to cause an additive machining device (such as a 3D printer) to form at least one of the periodic structures as per any one of the above described embodiments.

According to another aspect, there is provided a computer readable storage medium (such as a CAD file) having stored thereon the program element.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
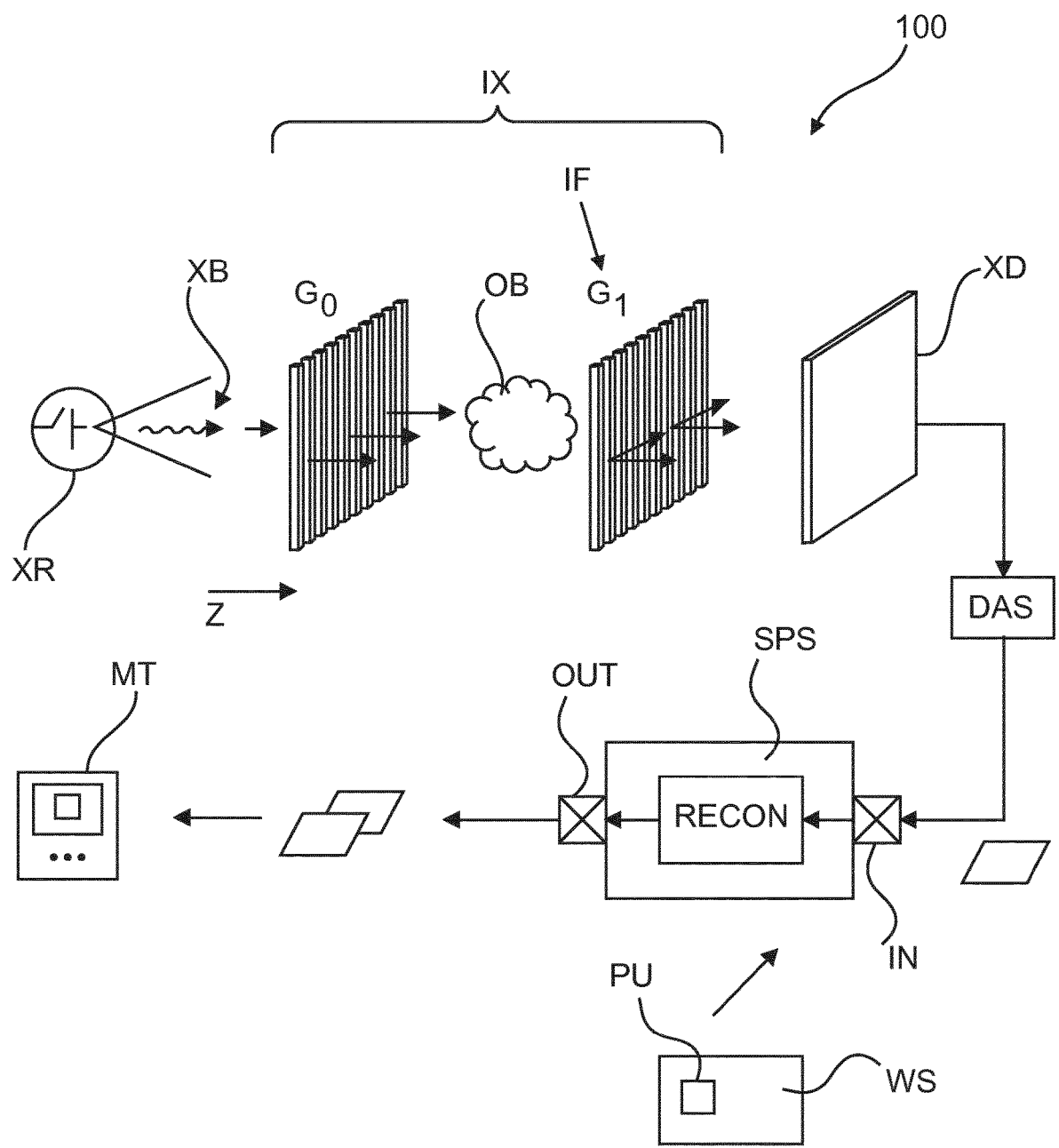
FIG. 1 is a schematic block diagram of an X-ray imaging arrangement including an X-ray detector and an interferometer.

With reference to FIG. 1 there is shown an imaging arrangement 100 comprising an X-ray imaging apparatus IX capable of producing imagery of an object OB. The X-ray imaging apparatus IX comprises an X-ray source XR and an X-ray sensitive detector XD. There is an examination region between the X-ray source XR and the X-ray detector XD in which resides the object OB to be imaged (or a part thereof).

The X-ray imager XI envisaged herein is primarily envisaged for medical applications such as diagnostic or navigation purposes in interventions but other, non-medical applications are not excluded herein. In other words, the object OB may be animate such as a human or animal patient or a part thereof (such as an anatomy of interest), or the object OB may be inanimate such as in security package screenings or non-destructive material testing, or other.

The optical axis and propagation direction of the imaging apparatus IX is indicated by Z in the Figure. The optical axis defines an imaging path along which the imaging takes place. In the above and in the following, spatial qualifiers such as "in front/behind", "downstream/upstream" or "under/above" etc., are always in relation to said optical axis Z, with direction from the X-ray source XR towards the detector XD.

The X-ray imaging apparatus envisaged herein may be of the rotatory or volumetric type such as a CT scanner where the optical axis Z can be changed to acquire projection detector signals from multiple directions to compute therefrom by suitable volumetric reconstruction schemes, 3D imagery internals of the object. However, volumetric imaging is not necessarily envisaged in all embodiments, but simpler, planar radiography apparatus embodiments are also envisaged herein, where the optical axis Z remains stationary.

The X-ray imaging apparatus IX as envisaged herein is configured for i) phase contrast and/or ii) dark field and/or iii) absorption imaging (collectively or singly (for any one of the three) or for any two of the three i)-iii), we shall refer to the related imagery as grating-based (in particular interferometric) imagery, in short "(T,D,$\phi$)-imagery"). To this end, the X-ray imaging apparatus IX includes a grating arrangement, such as an interferometer IRF, arranged with the object OB in the examination region. In particular, the proposed imaging apparatus IX includes, as the interferometer IRF, a single interferometric phase grating, referred to herein as G1. This is unlike other interferometric setups proposed for instance in F. Pfeiffer et al that use an additional (absorber) grating, G2. There is no second, discrete, absorber G2 grating required in the X-ray imaging apparatus IX as envisaged herein. Although in the following and above reference is made to "interferometric imaging" with the interferometer IF, it is understood that this is merely one embodiment of grating-based imaging and that other grating based imaging techniques are also envisaged herein, such as coded aperture imaging (such as reported by A. Olivo et al, "A coded-aperture technique allowing X-ray phase contrast imaging with conventional sources", Appl. Phys. Lett. 91 (2007)) or others.

In the proposed system, the single phase grating G1 of the interferometer IRF includes periodic structures in the form of grooves or trenches. In one embodiment these are cut or etched by wet or DRIE (Deep reactive-ion etching) or other suitable manufacturing purposes into a wafer of silicon. The periodicity (distance between any two neighboring grooves) or "pitch" is designated by g1 and is about 4 µm in one embodiment, but this depends on the mean energy of the beam XB and/or its brilliance or other factors as will be explained in more detail below.

In use, the single phase grating G1 is positioned either in front or behind the object OB in the examination region. The X-ray source XR operates to generate an X-radiation beam XB that interacts with the object and the interferometer IRF, that is, grating G1. After interaction, the radiation is detected at X-ray detector in the form of electrical signals. The electrical signals are digitized by a data acquisition system DAS and forwarded to an input interface IN of a signal processing system SPS. The signal processing system SPS processes these signals into imagery which is then output through port OUT for display on a monitor MT or for storage, or for other processing. Specifically, the signal processing system includes an image reconstruction functionality RECON which will be described in more detail below. The reconstruction functionality RECON allows processing the received detector signals into the phase-contrast and/or dark-field and/or transmission imagery. The signal processing system SPS may be integrated into the imaging apparatus IX or may run remotely therefrom on a workstation WS associated with the imager IX. Specifically, the proposed signal processing system SPS may run as a software routine on the imager XI or on the workstation WS or on a server in a cloud supported environment. The proposed SPS system may be implemented as hardware, specifically in circuitry, such as in a dedicated chip, for instance, by suitable programming as an FPGA. Hardwired chip implementations are also envisaged. The chip may be integrated in video or graphics hardware of the work station or may be integrated as a processing stage in the DAS, etc.

Turning now in more detail to the phase-contrast or dark-field imaging capability of the proposed X-ray imager, this is enabled in part by the interferometer IRF and in other parts by the detector XD, configured in a novel way. If the X-radiation supplied by the X-ray source XS is not natively coherent, an absorption grating G0 is arranged at the X-ray detector to convert the X-ray radiation beam into a plurality of coherent X-ray beams which then interact with the object OB and with phase grating G1. The source grating G0 at the source XR has a periodicity of g0. G0 is an absorption grating. It can be made by cutting or etching grooves or trenches into a wafer of silicon or other material as described above for the phase grating G1. But unlike the G1 grating, in the G0 grating its trenches are filled with high-Z materials such as gold, lead or other to confer its partial absorbing action. The filling can be done by electro-plating or other. The functional relationship between periods g0 and g1 are governed according to certain design rules such as $\lambda l/\gamma_0 g_0 \geq g_1$, with/being the distance between G0 and G1, $\lambda$ the mean wave length of the X-radiation, and $\gamma 0$ the ratio a source line of G0 width versus period g0.

The single grating G1 acts as a phase grating. In other words, it diffracts the incoming radiation by phase shifting (for instance by $\pi$) into diffraction fringe pattern that can be detected at the detector XD. Furthermore, at certain other distances, the phase modulation is transformed into an intensity modulation. These distances are called fractional Talbot distances. It is precisely at such a fractional Talbot distance d where the radiation sensitive layer XS of the detector XD is located.

As proposed herein, the radiation sensitive layer is structured so that intensities are captured through pixels covered with periodic structures at different phases. A simultaneous spatial sampling of the fringe positions in the fringe pattern is thereby affected. In other words, the function of the specially structured radiation sensitive layer XS is to translate the diffraction fringe pattern into an intensity modulation from which the phase of the impinging X-rays and the amount of scattering and, if desired, also the absorption can be determined, given a reference position of the fringes which can be established in an air scan when no object is present. Specifically, the intensity values captured at different phases form, for each image pixel, a phase curve which includes the desired interferometric image signals for any of the three channels of the (T,D,$\phi$)-imagery. Fourier analysis or related optimization methods can be used to extract this information as will be explained in more detail further below at FIG. 5.

As briefly mentioned above, earlier approaches in phase contrast imaging, such as reported by Pfeiffer et al use a Talbot-Lau interferometric arrangement IRF with the second grating G2 to sample the fringe pattern. Specifically, the sampling of the fringe pattern was done previously by scanning laterally, that is perpendicular to the optical axis Z, the said absorption grating G2 to so acquire, for each pixel, a series of intensity measurements in multiple X-ray exposures ("shots"). These measurements together define the respective phase curve for each pixel. In the context of coded aperture imaging, "G2" is a grating that has a duty cycle (defined as the fraction of X-ray sensitive to the X-ray insensitive area) varying from 0.5—which is a typical value for interferometric applications.

In radical departure from these approaches, and as mentioned initially, there is no individual, discrete phase grating G2 required in the setting proposed herein, but instead a fringe sampling functionality is now integrated into the X-ray detector XD. Dispensing with the G2 grating allows making the construction simpler because there is no mechanical arrangement required to scan the G2 grating, as has been previously done. Although earlier approaches existed that also dispense with scanning, the proposed scheme allows a more noise robust treatment and better image quality.

Also, as another advantage, the proposed imager allows acquiring the phase-contrast and dark-field imagery in a single X-ray exposure, rather than through a series of multiple exposure acquired during phase-step scanning in order to acquire the series of measurements, as in Pfeiffer et al.

In brief and to summarize, the X-ray detector XD, as envisaged herein, for use in the imaging apparatus IX, allows locally for each image pixel to acquire a plurality of intensities at different phases, thus making obsolete the scanning by phase stepping motion with additional absorption grating G2. This localized, single-shot multi-phase acquisition capability of the X-ray detector as envisaged herein will now be explained in more detail with reference to FIG. 2.

Figure 2A:
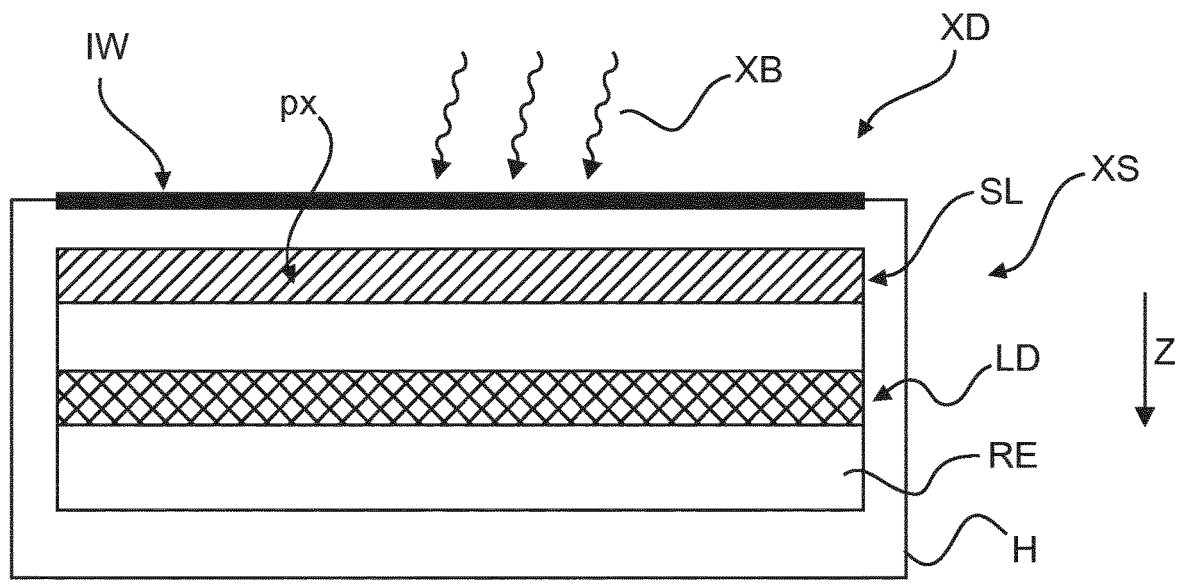
FIG. 2 are sectional views of the X-ray detector according to the two different embodiments.
Figure 2B:
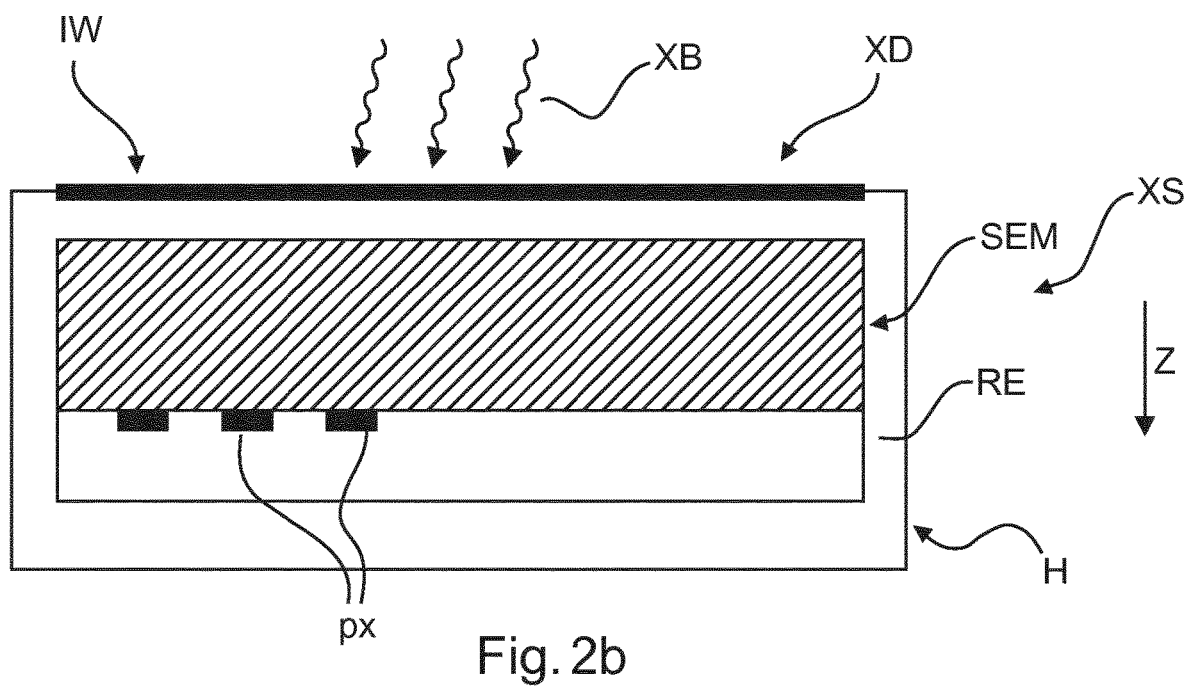

Specifically, FIGS. 2a,b present cross sectional views through the X-ray detector XD, the section plane in each view being parallel to the optical axis Z. FIG. 2a shows a detector XD of the indirect conversion type whilst FIG. 2B shows a detector XD in a different embodiment, namely of the direct conversion type. Generally, each detector type includes a radiation sensitive component XS that acts like a transducer to change the nature of the impinging X-radiation. For example, the X-radiation may be changed into a different type of radiation or into a charge or other. Although both detector types are envisaged herein in different embodiments, the detector XD of the indirect conversion type in FIG. 2a is preferred, to which we turn first.

Inside a detector housing H are arranged multiple layers. The face of the housing H, that is proximal to the detector source XB, includes an ingress window IW to admit the radiation XB (that has interacted with the interferometer IRF and the object OB) into the inside of the housing H. Radiation sensitive layers are arranged inside the housing with a scintillation layer SL being proximal and under it a layer LD of photodiodes, e.g. of a-Silicon or similar. The bottom layer is formed by readout circuitry RE, for instance in form of an array of TFTs or other.

The scintillation layer SL is made from crystals (e.g., Caesium Iodide (CsI) or other) that are grown to define a pixilation PX within the scintillation layer. Upon exposure to X-radiation beam XB, photons of visible lights are released by the scintillation layer SL and propagate downwards to be detected at respective locations by respective one of the photodiodes LD. The photodiodes LD convert the visible light into electrical signals which are then read out by the read-out electronics RE and passed on to the DAS and processed as described above in relation to FIG. 1. Instead of photodiodes, a CCD (charge-coupled device) sensor layer may be used in which case no TFT array may be required in the RE layer.

In the detector XD of direct conversion type in FIG. 2*b* there is no scintillation layer but the X-radiation sensitive component XS is now a semiconductor layer SEM (e.g., of a-Selenium or other) that is sandwiched between electrodes, with the anode being arranged on top and the cathodes being arranged distal under the semiconductor layer SEM (the electrodes are not shown in the Figure). The cathodes define the pixilation PX and are connected to the readout electronics RE. A voltage is applied across the semiconductor layer XS. Photons in the X-radiation beam XB penetrate into the semi-conductor layer SEM and cause cloud charges of holes and electrodes to form within the semiconductor layer SEM. The holes drift towards the cathodes whilst electrons drift to the anodes thereby causing an electrical signal which is registered by the readout electronics RE and processed as described above at FIG. 1.

The pixilation in the direct conversion type is given by an arrangement pattern of the electrodes (in particular the cathodes) whilst the pixilation in the detector of the indirect conversion type in FIG. 2*a* is given by the way the crystals are grown in the scintillation layer SL.

Turning now first to the indirect conversion type in FIG. 2A, it is envisaged herein in a preferred embodiment to include the fringe sampling functionality into the radiation sensitive component XS inside the detector's housing H. In one embodiment the fringe sampling functionality is built in or integrated into the scintillation layer SL itself. As mentioned earlier the fringe sampling functionality corresponds to an absorption grating with periodicity g2 embodied as suitable geometric structures having that periodicity. The periodicity in the scintillation layer is preferably half of the phase grating in G1 times the magnification of G1 to G2 for a π-phase shift grating. Alternatively, the fringe sampling functionality may be included as suitable periodicities at the required period in the photodiode layer LD.

Alternatively, if a direct conversion type is used as per FIG. 2B, the periodicities may be imprinted in the semi-conductor layer XS, where the electric charge clouds are generated. Preferably, software or hardware-based functionalities are used to reduce charge-sharing effects.

To explain in more detail the fringe sampling functionality of the radiation sensitive component XS of the X-ray detector XD as proposed herein, reference is now made to FIGS. 3 and 4.

Figures 3A, 3B:
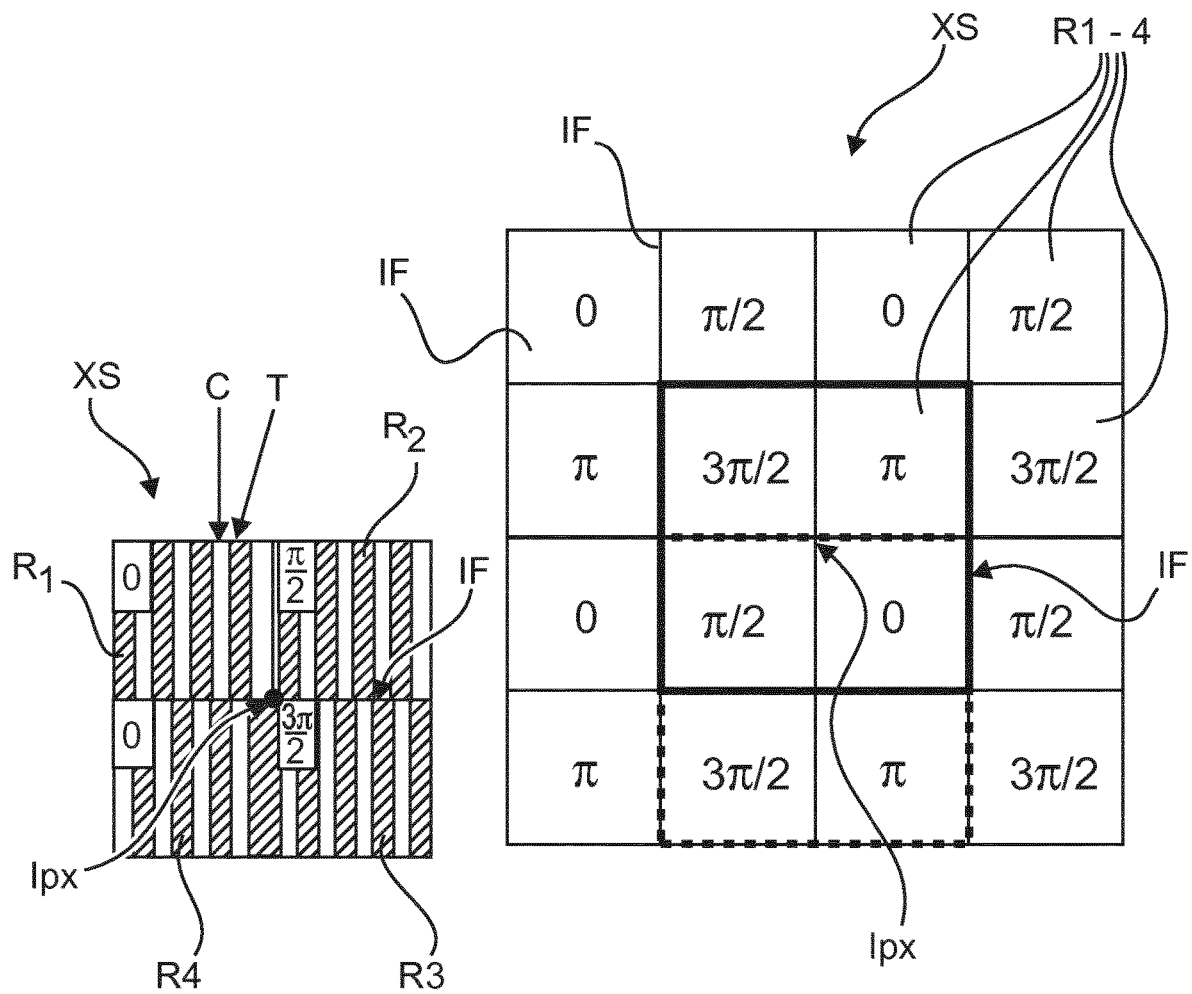
FIG. 3 shows a plan view of an X-ray sensitive component of the X-ray detector according to one embodiment.

Turning first to FIG. 3*a, b*, these show respective plan views (along the optical axis Z) of the respective radiation sensitive component SX as envisaged herein with the housing and other layers cut away. Specifically, FIG. 3*a* shows a section of the radiation sensitive component SX of FIG. 3*b*.

The radiation sensitive component XS, for instance the scintillation layer or semiconductor layer or other as mentioned above, is structured so as to have a periodicity g2. For the periodicity g2, Talbot design rules apply as per $g0=g2*l/d$. A suitable one d of the fractional Talbot distances now runs from the phase grating G1 down to the mentioned structuring of the radiation sensitive component XS inside the detector XD. In general, the period g2 is half of the period g1 of the phase grating G1 of the interferometer IRF times the magnification of G1 to G2 for a π-phase shift grating. For a π/2 phase shift gratings, the period g2 equals g1.

The radiation sensitive layer SX is tessellated (not necessarily in whole) into a number of regions Rj, of which four are shown labelled R1-R4 in an exemplary embodiment of FIG. 3*a*. All those regions Rj meet or are joined at respective interfaces IF. Each of the regions has the same periodicity g2, but at different phases relative to each other. For instance, the "phase region" R1, as it may aptly be called in the upper left part of FIG. 3*a*, has the g2 periodicity at a certain reference phase, say "0", whilst the other three neighboring regions R2-R4 have the same periodicity but shifted (geometrically) by π/2, π or 3π/2, respectively, relative to phase 0 of the first mentioned phase region R1. This 2×2 phase structure, or super- or combo-multi-phase-region, may then be repeated across the remainder of the surface of the layer SL. Two of such (in this case 2×2) super-regions are shown bordered in bold and dashed lines, respectively, in FIG. 3*b*.

Preferably it is envisaged that the entire surface of the radiation sensitive layer XS is tessellated (or partitioned) so that each location on said surface falls into exactly one of the phase regions Rj but this may not necessarily be so in all embodiment, where some sections of the layer XS remain unstructured. Preferably, but not necessarily so in all embodiments, each of the regions Rj is sized to cover exactly one and only one detector pixel PX which is given by the hardware of the detector arrangements as explained earlier at FIG. 2. Alternatively, some or all of the regions Rj may cover respective groups of two or more of such native hardware pixels PX.

Having the radiation sensitive surface tessellated into regions Rj of different phase allows for a simultaneous read-out with a single X-ray exposure of all the required intensity information under different phases, for which earlier a phase stepping operation was needed as in Pfeiffer et al. To this end, and in some embodiments of the present arrangement, virtual image pixels IPX are defined, whose locations do not coincide with that of any of the native pixels PX. For instance, in the 2×2 arrangement in FIG. 3*a*, the image pixel IPX is defined by the location of the common vertices of the four rectangular, in particular square shaped, regions Rj.

The (T,D,ϕ)-signals may be reconstructed for this virtual image pixel location IPX by processing all the intensities as supplied by the pixels under the surrounding regions R1-R4 which due to their different phase arrangements have acquired the intensities under different phases, similar to a four step phase stepping operation in the conventional Pfeiffer et al setup. Because the location of virtual image pixel IPX is different from the location of the surrounding detector pixels PX under the surrounding regions Rj, there is a slight angular error when using the surrounding detector pixels for the intensity values readings when computing the image values, but this error has been found to be negligible. Still, to keep this error within a reasonable margin, it is preferable not to make the super-regions too large. Preferably, the detector pixels within each super-pixel should be within 1 or 2 detector pixel PX widths of the image pixel location IPX.

The structuring of the radiation sensitive layer into the periodicities g2 of Regions Rj may be done by forming (by any type of subtractive machining) grooves or trenches into the X-radiation sensitive layer (eg, scintillation layer SL or semiconductor layer SEM or other), to so locally disable the X-ray sensitive component XS. In this manner each region Rj has the same periodicity defined by an alternating sequence of X-ray sensitive sections C and X-ray insensitive T sections, but at different relative phases. Alternatively, and conversely, one may use an X-ray insensitive base material and locally add X-ray sensitive elements. Alternatively still, a similar structuring may be formed in the photodiode layer DL.

Instead of the above described subtractive machining, the periodic structures in the regions Rj may be formed by additive manufacturing such as 3D printing, in layers, lines or voxelwise. The geometric description of the periodic structure and the tessellation are encoded in a file, such as CAD file or other. The description is rendered into commands which are then used to control operation of the 3D printer or other additive manufacturing device.

The X-ray insensitive sections T are shown in FIG. 3a as greyed out stripes, whilst the X-ray sensitive sections C, which are the sections between any two T's, are shown clear. The X-ray sensitive sections C are the interspaces that are left between any two neighboring X-ray insensitive sections T. The same form processing can be applied to each of the regions, however, each time the phase of the periodicity is respectively shifted by a phase shift amount. Preferably the phase shifts for each region Rj are equally distributed across a full phase $2\pi$, so the phase shift amount is $2\pi/K$, whilst K defines the number of neighboring phase regions Rj. For instance, in FIGS. 3a,b the super-phase region is a 2×2 structure so there are four neighboring regions for each imaging pixel IPX. For the 2×2 super-region arrangement with four different (sub-)phase regions R1-R4, the full period $2\pi$ is divided into four equal phase shifts that is 0, $\pi/2$, $\pi$, $3\pi/2$, one for each of the neighboring phase regions in the super-region. The 2×2 pattern of neighboring regions are then repeated as mentioned preferably throughout the entire surface of the radiation sensitive layer SL to so define the tessellation. An uneven phase distribution across regions Rj for some or all super-regions may also be envisaged in the alternative.

From the above it will be understood that due to the conception and location of the imaging pixels IPX, the reconstructed phase contrast or dark field image will in general be smaller than the full field view of the detector due to a missing border portion.

Figure 4A:
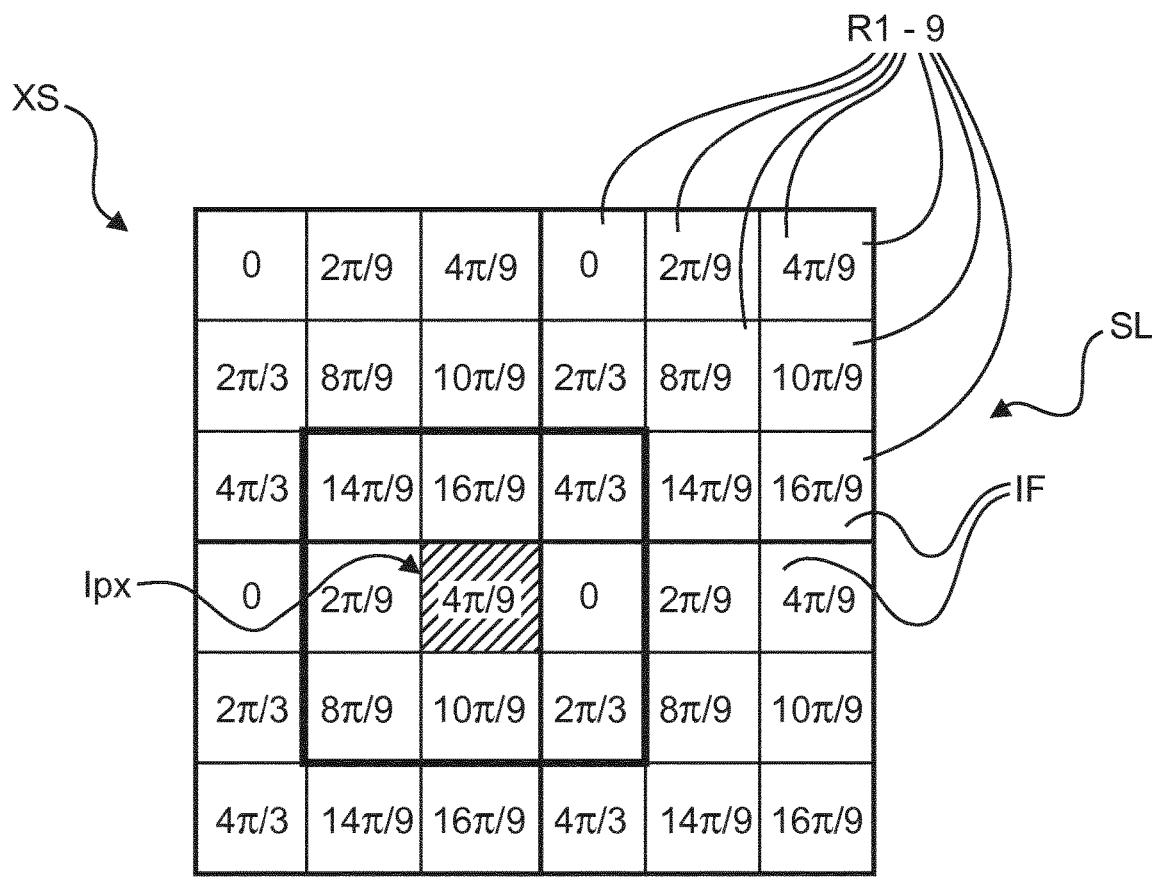
FIG. 4 shows further embodiments of the radiation sensitive component in plan view.

FIG. 4 shows plan views of alternative arrangements of phase regions $R_j$ across the surface of the radiation sensitive layer/component XS. For instance, FIG. 4a shows 3×3 super/region arrangement into nine neighboring regions R1-R9 whilst the relative phase shifts are fractions of $2\pi/9$, although uneven phase shift amounts are also envisaged here. It will be understood that in comparison to the FIG. 3a arrangement, the image pixel IPX in FIG. 4a now does correspond to a respective hardware pixel position PX, for instance the shaded region "$4\pi/9$" at the center of the 3×3 super/region bordered by bold lines. This would be the case for any super-region with odd edge length $(2k+1)*(2k+1)$, $k \geq 1$ (whilst for even edged super-regions the image position IPX would not generally correspond to hardware pixel PX position). In the case of 3×3 super-regions, made up of 9 phase regions R1-R9, the respective phase contrast or dark field signal is reconstructed for image pixel IPX based on intensity readings at different phases from pixels PX of the eight surrounding regions (each having a different phase) of the 3×3 block and the center pixel where the image pixel IPX is located.

The embodiments in FIG. 3a, b and FIG. 4a can be extended mutatis mutandis to any block arrangement N×N of super-regions, but, keeping in mind the earlier mentioned error margin, N can be expected to be less than 5 for most practical applications. Preferably, each image pixel IPX, which may or may not coincide with a true hardware pixel location PX, should be associated with neighboring phase regions that have at least three different phases to allow unambiguously specifying the respective phase curve and to so secure better reconstruction results of the (T,D,φ)-imagery. Preferably for each image pixel IPX is surrounded by different phase regions at different phases. Yet more preferably, the super-regions for each image pixel IPX are so arranged that each region Rj within the super-region has a different phase. This makes the image processing robust against noise. In principle, the more regions Rj with different phases around a given image pixel IPX, the more accurate the definition of the phase curve and hence the more accurate the reconstruction of the (T,D,φ)-imagery. As mentioned, 3 different phases are preferable, although two may also suffice in some special cases, for instance if it is known upfront that the dark-field signal is zero. Preferably, the number of different phase regions Rj neighboring a given image pixel IPX is about 3-9.

Figure 4B:
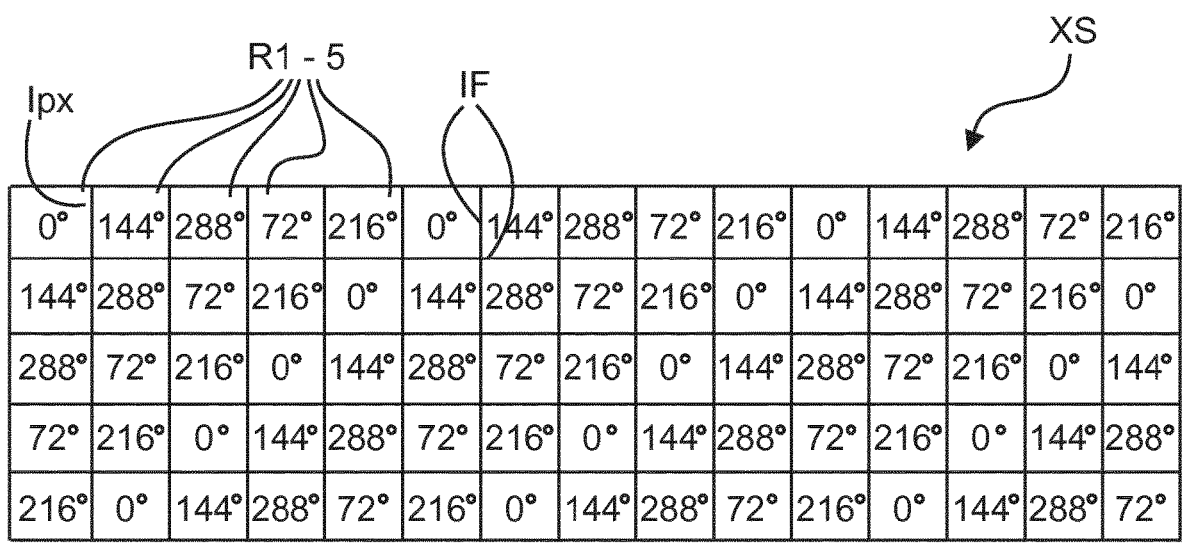

The arrangement of FIG. 4b shows a different embodiment, with five different phase regions R1-R5 arranged in different runs, each run five regions long, at different phases arranged one after the other repeating in each row whilst shifted by one or more phases relative to each other across different rows (the structure may also be transposed with rows and columns interchanged). Runs of other than 5 are also envisaged and the number of rows may also differ from 5. Preferably, the number of runs equals the number of rows. The number of runs in each row, the length of the runs and the number of rows/columns will depend on detector size requirements. The numbers in FIG. 4b indicate five exemplary phases, 0°, 72°, 144°, 216° and 288°. These are distributed in the runs so that any two neighboring regions have a relatively large phase difference. In the particular arrangement of FIG. 4b, the phase difference is 144°. In general then, and according to one embodiment, for any given sequence of phases $\alpha_k$, a distribution among the regions Rj's is preferred such that phase difference is maximized for at least two neighboring regions Rj.

It can be seen, that the super-regions in the FIG. 4b embodiment are 1D (linear) rather than 2D in FIG. 3 and FIG. 4a.

In the embodiment of FIG. 4b, no two neighboring regions have the same phase. The tessellation in the FIGS. 3,4a fulfills the more stricter requirement that there are no two neighboring region $R_{j,k(j \neq k)}$ that have the same phase, across interface and diagonally across vertices. The phase distribution among the regions Rj in FIG. 4b is exemplary and other distributions may be used instead.

The arrangements in FIG. 4b may be suitable for CT, in particular for reconstruction with sliding window techniques as per I. Zanette et al or similar. The arrangements in FIG. 3 and FIG. 4a may be more suitable for radiography imaging where full-view (FoV) detectors are used which may not be the case for CT where the detectors are arranged in a few detector lines not necessarily covering as such the whole FoV. The arrangement in FIG. 4b in runs affords efficient manufacturing as compared to the design in FIG. 3 and FIG. 4a.

In tomographic applications, the proposed multi-phase structuring allows spatial phase stepping across adjacent pixels and this can be advantageously combined with an angular phase stepping in the sliding window technique. A further combination with IBSIR reconstruction is even more advantageous as this allows for a noise robust sampling pattern for CT.

For simple manufacturing, the phase regions Rj are preferably rectangles or squares although other, preferably regular, polygon shapes are not excluded herein such as triangle, pentagon, hexagon. Irregular polygons may be called for in other embodiments although manufacturing costs may be higher. Shapes other than polygonal, such as curvilinear (e.g., circular) may also be envisaged for the regions Rj, and so are combinations of any of these shapes. Equally, the shapes of the super-regions may also have any suitable polygon or curvilinear shape or a combination thereof.

As a further extension of the above, not all region Rj shapes may be equal. In other words, tessellations in different shapes are also envisaged. The same applies to the shapes of the super-regions, which may not necessarily be equal across the whole surface XS but may differ among each other. A yet further extension of the above, the shapes or shape types of the super-regions may differ from the shapes or shape types of their regions Rj. For instance, in FIG. 3 and FIG. 4a, the regions are squares and so are the super-regions N×N. However, this may not be so in all embodiments, such in FIG. 4b where the aspect ratio for the region rectangles Rj is different from the aspect ratio of the long super-region rectangle. In other embodiments, the super regions may be rectangular or of any other shape whilst the regions are still square or of any other shape than that of the super-region.

In order to correctly assign the various intensity readings for different phases to each image pixel, there is a signal grabber component (not shown) that associates for each image pixel position the respective hardware pixel locations in the respective super-region (e.g., N×N block). This can be implemented by a look-up table. In other words, the super-regions are conceptual and define a specific sampling pattern. The grabber is used to implement the sampling pattern. The grabber may be reconfigurable so that the size of super-region may be changed (in particularly reduced) upfront or dynamically during signal processing. The sizes of the super-regions may remain constant or may be varied for any given processing.

Figure 5:
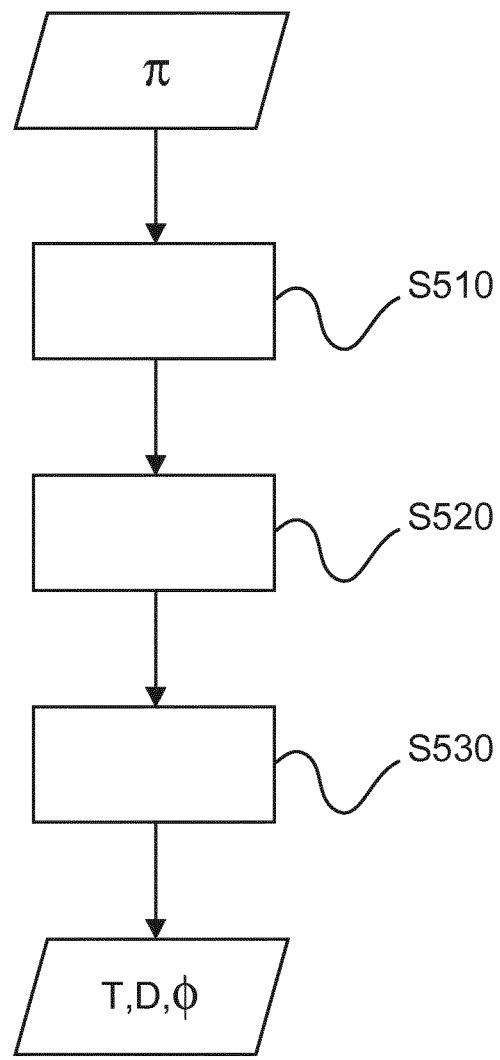
FIG. 5 is a flow chart of a signal processing method for dark field and/or phase contrast imaging and/or transmission imaging.

Reference is now made to the flow chart in FIG. 5 to explain in more detail method steps that underlie operation of the reconstructor RECON when processing data captured by the proposed detector XD. More particularly it will be explained in more detail how the different intensities captured at different phases can be combined to compute the "(T,D,φ)-imagery, that is, in particular, the phase contrast image signal and/or the dark field image signal and/or, if desired, the absorption/transmission signal image. It will be further understood that the processing steps described below in relation to the method is not necessarily tied to the architecture given above in FIGS. 1-5 but the following method steps may also be construed as a teaching in their own right.

At step S510 detector readings from detector XD of an X-ray imaging apparatus is received. These readings are derived from imaging signals, acquired at the detector XD, whilst a plurality of periodic structures were present in the imaging path (that is, along the optical axis Z) during exposure of the X-ray detector with X-radiation. The X-radiation has furthermore passed through an interferometer IRF and an object OB to be imaged before being detected by the X-ray detector XD. In one embodiment and preferably envisaged herein the periodic structures are formed by the multi-phased regions integrated in the X-ray detector XD's X-ray sensitive component XS as explained above with reference to FIGS. 3 and 4. Each image pixel position IPX denoted as j is hence associated with multiple three or more intensity measurements i as detected under different phases in the respective phase regions $R_j$ around the respective pixel position j. These intensity measurements form the respective phase curves for each pixel, and will be denoted herein as $m_{ij}$.

At step S520 the measurements $m_{ij}$ are then processed per pixel j in the phase retrieval scheme which can be formulated as a per-pixel optimization problem for each image pixel j as $$\Delta(T, D, \phi) = \sum_j \frac{1}{\sigma_{ij}^2} (m_{ij} - T_j A_{ij}(1 + D_j V_{ij} \cos(\phi_j + \alpha_{ij})))^2 + \lambda R(T, D, \phi) \quad (1)$$

where $T_j$, $D_j$, and $\phi_j$ are the desired values for transmission, dark-field signal, and phase shift caused by the object, $m_{ij}$ are the different measurements related to this image pixel. The quantities $A_{ij}$, $V_{ij}$, and $\alpha_{ij}$ are the blank scan intensities, visibilities, and fringe phases. $\sigma_{ij}$ is the standard deviation of the measurement $m_{ij}$ The above optimization in terms of a cost function $\Delta$ as of equation (1) includes an implicit smoothing scheme by using a regularization term R—a functional component—in the optimization formulation so as to penalize changes. The proposed regularization acts in particular in the dark field signal channel and the phase contrast channel and/or the transmission channel. The smoothness regularization helps compensate for the inherent sub-sampling due to there being only one measurement i per image pixel j. This is then essentially under-determined problem and the proposed implicit smoothing per channel regularization helps to resolve this. It is also of note that the super-regions (or super-pixel) in the multi-phase structures Rj as proposed above is in itself a smoothing, but a brute force which is undesired. The added smoothness constraint R configured for per channel regularization helps to balance this and adds robustness.

The optimization (1) is to fit the image channel variables T,D,φ (transmission T, dark field D and phase φ) to the measurement $m_{ij}$ so as to minimize the square sum. Other objective function formulations where other expressions are to be minimized or maximized are also envisaged. It will be understood that in order to solve the optimization problem when fitting the measurements to the three image channel variables T,D,φ, any suitable numerical optimization scheme may be used such as conjugate gradients, steepest descent, iterative coordinate decent, and others. It will also be understood to properly account for the three effects of absorption, scattering and refraction the three imaging variables T,D,φ should be preferably fitted together in the optimization scheme to so properly separate the three signals to avoid cross talk among any two of them.

A number of different embodiments for the regularization term is envisaged herein with λ indicating the regularization strength which is any positive number, which can be adjusted through analysis of the cost function, e.g. by analyzing the residuum of the cost function, similar to what P. C. Hansen et al report in "Exploiting Residual Information in the Parameter Choice for Discrete Ill-Posed Problems", BIT Numerical Mathematics, Vol 46, Issue 1, pp 41-59, March 2006. Other cost function residual based approaches are also envisaged herein.

Specific embodiments for the regularization function $\lambda R(T,D,\phi)$ as envisaged herein, include the following:

In one embodiment, a total variation minimization is used, independently for each image channel:

$$\Delta(T, D, \phi) = \sum_j \frac{1}{\sigma_{ij}^2}(m_{ij} - T_j A_{ij}(1 + D_j V_{ij} \cos(\phi_j + \alpha_{ij})))^2 + \qquad (2)$$

$$\lambda_T \sum_j \|\nabla T_j\|^2 + \lambda_\phi \sum_j \|\nabla \phi_j\|^2 + \lambda_D \sum_j \|\nabla D_j\|^2$$

In expression (2) and below, "$\| \|$" indicates a suitable norm configured to measure smoothness through the respective channel gradient. "$\| \|$" may indicate absolute values (1-norm) but other norms such as Euclidean, or p-norms (p>2), or combinations thereof, or others are also envisaged herein.

In another embodiment, a total variation minimization is used, independent for each channel, but total variation is imposed on the integrated phase $\Phi$ rather than the differential phase $\phi$:

$$\Delta(T, D, \phi) = \sum_j \sum_i \frac{1}{\sigma_{ij}^2}(m_{ij} - T_j A_{ij}(1 + D_j V_{ij} \cos(\partial_x \Phi_j + \alpha_{ij})))^2 + \qquad (3)$$

$$\lambda_T \sum_j \|\nabla T_j\|^2 + \lambda_\Phi \sum_j \|\nabla \Phi_j\|^2 + \lambda_D \sum_j \|\nabla D_j\|^2$$

In yet another embodiment, nuclear norm regularization is used on the attenuation image channel and the integrated phase channel, which promotes additionally similar gradients in these two images, where $w_T$ and $w_\Phi$ are normalization factors to weight the strength of the regularization on the two image channels:

$$\Delta(T, D, \phi) = \sum_j \sum_i \frac{1}{\sigma_{ij}^2}(m_{ij} - T_j A_{ij}(1 + D_j V_{ij} \cos(\partial_x \Phi_j + \alpha_{ij})))^2 + \qquad (4)$$

$$\lambda_{T\Phi} \sum_j \sqrt{\|w_T \nabla T_j\|^2 + w_\Phi \|\nabla \Phi_j\|^2 + 2\sqrt{w_T w_\Phi}\|\nabla T_j \times \nabla \Phi_j\|^2} +$$

$$\lambda_D \sum_j \|\nabla D_j\|^2$$

Other regularization functions $\lambda R(T,D,\phi)$ than total variation (TV) or nuclear norm regularization are also envisaged in the alternative, for instance Huber regularization, higher order TV, and/or alike can be used. Combinations of these or other different regularization terms are also envisaged.

All that those regularization terms have in common is that they solve the sub-sampling problem by smoothing as explained above.

Another benefit of the proposed phase retrieval scheme is that the resolution of the images can be controlled independently. In particular, in an application to dark-field lung imaging, it might be desired to provide a transmission image at higher spatial resolution than the dark-field image. This can be achieved by imposing a stronger smoothness constraint on the dark-field image D by increasing the corresponding regularization strength.

In the conclusion of the optimization in step S520 preferably with the smoothing scheme as described above, the dark field image and/or the phase contrast image and/or, if desired, the transmission image may be output at step S530 for display or for further processing, storage etc.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, in particular a non-transitory storage medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A component for an X-ray detector, comprising:
a layer tessellated in a plurality of different regions, the plurality of different regions having respective periodic structures at a respective phase,
wherein two neighboring regions of the plurality of different regions meet or are joined at respective interfaces, and have periodic structures at different phases.

2. The component according to claim 1, wherein any two neighboring regions of the plurality of different regions have periodic structures at different phases.

3. The component according to claim 1, wherein at least one given region of the plurality of different regions is at least partly surrounded by regions having different phases, and each of the different phases is different from the phase of the given region.

4. The component according to claim 1, wherein at least one region of the plurality of regions is a single pixel region.

5. The component according to claim 1, wherein the component is radiation sensitive.

6. The component according to claim 5, wherein the layer is at least one of a scintillation layer, a semiconductor layer, and a photodiode-layer.

7. The component according to claim 1, wherein the periodic structures are arranged as an alternating pattern of radiation insensitive and radiation sensitive elements.

8. An X-ray detector comprising the component according to claim 1.

9. The component of claim 1, wherein one region of the two neighboring regions includes first X-ray sensitive sections and first X-ray insensitive sections that are arranged alternately in a first direction,
the other one region of the two neighboring regions includes second X-ray sensitive sections and second X-ray insensitive sections that are arranged alternately in the first direction,
one section of the first X-ray sensitive sections meets with or is joined with one section of the second X-ray insensitive sections, and
one section of the first X-ray insensitive sections meets with or is joined with one section of the second X-ray sensitive sections.

10. An X-ray imaging apparatus, comprising:
an X-ray detector; and
a component comprising a layer tessellated in a plurality of different regions, the plurality of different regions having respective periodic structures at a respective phase,
wherein two neighboring regions of the plurality of different regions meet or are joined at respective interfaces, and have periodic structures at different phases.

11. A signal processing method for at least one of dark-field, phase contrast, and transmission imaging, comprising:
receiving readings from an X-ray detector within an imaging path of an X-ray imaging apparatus, having a component comprising a layer tessellated in a plurality of different regions, each of the plurality of different regions including at least one interface, two neighboring regions of the plurality of different regions meeting or being joined at respective interfaces, the two neighboring regions having respective periodic structures at different phases; and
processing the readings into at least one of dark-field, phase contrast, and transmission image signals, the processing including a regularization.

12. A non-transitory computer-readable medium having executable instructions stored thereon which, when executed by at least one processor, cause the at least one processor to perform a signal processing method for at least one of dark-field, phase contrast, and transmission imaging, the method comprising:
receiving readings from an X-ray detector within an imaging path of an X-ray imaging apparatus, having a component comprising a layer tessellated in a plurality of different regions, each of the plurality of different regions including at least one interface, two neighboring regions of the plurality of different regions meeting or being joined at respective interfaces, the two neighboring regions having respective periodic structures at different phases; and
processing the readings into at least one of dark-field, phase contrast, and transmission image signals, the processing including a regularization.

* * * * *